(12) United States Patent
Schweiss et al.

(10) Patent No.: US 9,220,486 B2
(45) Date of Patent: Dec. 29, 2015

(54) RECONSTITUTION AND APPLICATOR SYSTEM FOR WOUND SEALANT PRODUCT

(71) Applicants: BAXTER INTERNATIONAL INC., Deerfield, IL (US); BAXTER HEALTHCARE SA, Glattpark (CH)

(72) Inventors: Mark Schweiss, Grayslake, IL (US); Atif M. Yardimci, Lake Forest, IL (US); Scott R. Ariagno, Palatine, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 94 days.

(21) Appl. No.: 14/143,387

(22) Filed: Dec. 30, 2013

(65) Prior Publication Data

US 2014/0114276 A1    Apr. 24, 2014

Related U.S. Application Data

(62) Division of application No. 12/877,889, filed on Sep. 8, 2010, now abandoned.

(60) Provisional application No. 61/240,586, filed on Sep. 8, 2009.

(51) Int. Cl.
*A61B 17/03* (2006.01)
*A61B 17/00* (2006.01)
(Continued)

(52) U.S. Cl.
CPC ......... *A61B 17/00491* (2013.01); *A61J 1/2093* (2013.01); *B01F 5/0685* (2013.01);
(Continued)

(58) Field of Classification Search
CPC ............... A61B 17/00491; A61B 2017/00495; B01F 5/0688; B01F 13/002; B01F 5/0685; B01F 13/0023; B01F 15/0201; B01F 5/0693; B01F 15/0225; A61J 1/2093; A61J 1/2089
USPC ............ 606/213, 214, 215, 216, 82–91, 190, 606/231, 30, 31, 246, 247, 256, 537, 252, 606/403, 405, 406, 416
See application file for complete search history.

(56) References Cited

U.S. PATENT DOCUMENTS

| 3,861,652 A | 1/1975 | Clark et al. |
| 4,127,131 A | 11/1978 | Vaillancourt |

(Continued)

FOREIGN PATENT DOCUMENTS

| WO | WO-96/39212 A2 | 12/1996 |
| WO | WO-01/70178 A2 | 9/2001 |

(Continued)

OTHER PUBLICATIONS

Floseal Hemostatic Matrix, 10mL Instructions for Use (published more than one year before Sep. 8, 2009).

*Primary Examiner* — Jing Ou
(74) *Attorney, Agent, or Firm* — Marshall, Gerstein & Borun LLP (57) ABSTRACT

A system for mixing or reconstituting agents including engageable syringe barrels, one of which having a male engagement region and the other a female engagement region. Each of the male and female engagement regions is provided with a screen. The screens are closely spaced from one another when the first and second syringe barrels are engaged with one another. The screens may take the form of a mesh, a plurality of protuberances, or cantilevered wedges having tapering thicknesses.

6 Claims, 12 Drawing Sheets

(51) Int. Cl.
  *B01F 5/06* (2006.01)
  *B01F 13/00* (2006.01)
  *B01F 15/02* (2006.01)
  *A61J 1/20* (2006.01)

(52) U.S. Cl.
  CPC ............ *B01F5/0688* (2013.01); *B01F 5/0693* (2013.01); *B01F 13/002* (2013.01); *B01F 13/0023* (2013.01); *B01F 15/0201* (2013.01); *B01F 15/0225* (2013.01); *A61B 2017/00495* (2013.01); *A61J 1/2089* (2013.01)

(56) References Cited

U.S. PATENT DOCUMENTS

| | | | |
|---|---|---|---|
| 4,631,055 A | 12/1986 | Redl et al. | |
| 4,743,229 A | 5/1988 | Chu | |
| 4,846,405 A | 7/1989 | Zimmermann | |
| 4,978,336 A | 12/1990 | Capozzi et al. | |
| 5,209,776 A | 5/1993 | Bass et al. | |
| 5,368,563 A | 11/1994 | Lonneman et al. | |
| 5,425,580 A | 6/1995 | Beller | |
| 5,443,183 A | 8/1995 | Jacobsen et al. | |
| 5,474,540 A | 12/1995 | Miller et al. | |
| 5,522,804 A | 6/1996 | Lynn | |
| 5,582,596 A | 12/1996 | Fukunaga et al. | |
| 5,605,255 A | 2/1997 | Reidel et al. | |
| 5,665,067 A | 9/1997 | Linder et al. | |
| 5,772,665 A | 6/1998 | Glad et al. | |
| 5,788,670 A | 8/1998 | Reinhard et al. | |
| 5,957,166 A | 9/1999 | Safabash | |
| 5,989,215 A | 11/1999 | Delmotte et al. | |
| 6,132,396 A | 10/2000 | Antanavich et al. | |
| 6,234,196 B1 | 5/2001 | Fischer et al. | |
| 6,267,154 B1 | 7/2001 | Felicelli et al. | |
| 6,302,160 B2 | 10/2001 | Castellano | |
| 6,305,413 B1 | 10/2001 | Fischer et al. | |
| 6,328,229 B1 | 12/2001 | Duronio et al. | |
| 6,454,739 B1 | 9/2002 | Chang | |
| 6,461,325 B1 | 10/2002 | Delmotte et al. | |
| 6,585,696 B2 | 7/2003 | Petersen et al. | |
| 6,620,125 B1 | 9/2003 | Redl | |
| 6,723,131 B2 | 4/2004 | Muschler | |
| 6,835,186 B1 | 12/2004 | Pennington et al. | |
| 6,965,014 B1 | 11/2005 | Delmotte et al. | |
| 7,135,027 B2 | 11/2006 | Delmotte | |
| 7,763,269 B2 | 7/2010 | Wright et al. | |
| 7,766,919 B2 | 8/2010 | Delmotte | |
| 7,819,846 B2 | 10/2010 | Lee | |
| 7,862,538 B2 | 1/2011 | Sawhney et al. | |
| 2001/0016703 A1 | 8/2001 | Wironen et al. | |
| 2001/0018598 A1* | 8/2001 | Cruise | A61B 17/00491 606/214 |
| 2002/0049405 A1* | 4/2002 | Deslauriers | A61B 17/8827 604/82 |
| 2002/0055708 A1 | 5/2002 | Peterson | |
| 2002/0072703 A1 | 6/2002 | Nollert et al. | |
| 2002/0101785 A1 | 8/2002 | Edwards et al. | |
| 2003/0195489 A1 | 10/2003 | Peterson | |
| 2004/0127846 A1* | 7/2004 | Dunn | A61J 1/2089 604/82 |
| 2005/0209555 A1 | 9/2005 | Middleton et al. | |
| 2006/0191962 A1 | 8/2006 | Redl et al. | |
| 2007/0203475 A1 | 8/2007 | Fischer et al. | |
| 2009/0038701 A1 | 2/2009 | Delmotte | |
| 2009/0198177 A1* | 8/2009 | Sawhney | A61B 17/0057 604/82 |
| 2010/0246316 A1 | 9/2010 | Delmotte | |
| 2010/0274279 A1 | 10/2010 | Delmotte | |
| 2011/0060361 A1 | 3/2011 | Schweiss et al. | |

FOREIGN PATENT DOCUMENTS

| | | |
|---|---|---|
| WO | WO-2005/016442 A1 | 2/2005 |
| WO | WO-2005/018831 A1 | 3/2005 |
| WO | WO-2005/048977 A2 | 6/2005 |
| WO | WO-2005/065668 A2 | 7/2005 |

* cited by examiner

RECONSTITUTION AND APPLICATOR SYSTEM FOR WOUND SEALANT PRODUCT

REFERENCE TO RELATED APPLICATIONS

Pursuant to 35 U.S.C. §120, this application claims priority to U.S. patent application Ser. No. 12/877,889, now abandoned. The entirety of U.S. patent application Ser. No. 12/877,889 is incorporated herein by reference. Pursuant to 35 U.S.C. §119(e), this application claims the benefit of the filing date of U.S. Provisional Application No. 61/240,586, filed Sep. 8, 2009, the entirety of which is incorporated herein by reference.

BACKGROUND

Field of the Disclosure

This disclosure relates generally to systems for applying a sealant to a work surface and, more specifically, to a system for mixing or reconstituting components of a two-component tissue sealant and delivering the mixed components into and through a cannula for delivery to a tissue site, or directly from a syringe to a tissue site.

BRIEF SUMMARY OF THE DISCLOSURE

It is known to mix or reconstitute components of sealants prior to introduction into a tissue wound site. For instance, a known technique for preparing thrombin and fibrinogen for use as a tissue sealant is to pull thrombin in a liquid form from a bowl into a large bore syringe barrel, dock the large bore syringe barrel with another syringe containing a dry hemostatic matrix powder, and mix the contents of the two syringes. A large bore syringe reduces the force necessary to reconstitute the contents of the docked syringes (such as by pouring the contents back and forth between the two syringes). However, a standard large bore syringe will undesirably permit thrombin to drain back into the bowl.

It is also challenging to efficiently mix the contents of the two syringe barrels when docked with one another. The hemostatic matrix tends to form clumps of material which hinder the ability to prepare a homogeneous mixture. The system of the present disclosure achieves reliable retention of dry powdered agents to be reconstituted, such as lyophilized thrombin, and also allows more efficient and homogenous mixing of a diluent and the powdered agent to be reconstituted.

DETAILED DESCRIPTION OF THE PREFERRED EMBODIMENTS

The system of the present disclosure includes a first syringe barrel 10 and a second syringe barrel 12. The first syringe barrel 10 includes a male engagement region 14 and the second syringe barrel 12 includes a female engagement region 16. The male engagement region 14 and the female engagement region 16 may each be provided with a screen 18, 20 that serves to partially seal the respective barrel interior. In a first embodiment, the screen 18, 20 may take the form of a mesh screen with a plurality of round openings 22. The openings 22 may all be of equal size, or may be of varying sizes. Each of the screen 18, 20 serves to retain fluid in the respective syringe barrel 10, 12 even when uncapped and unengaged. The screens 18, 20 also serve as mixing elements that aid in expediting the mixing of contents passing through the openings 22. It is found that tissue sealant constituents of relatively low viscosity, such as thrombin, can be reconstituted with a lower number of pours or swooshes when being mixed between the first and second syringe barrels 10, 12 of the present disclosure, as compared with conventional syringe barrels.

Figure 2:
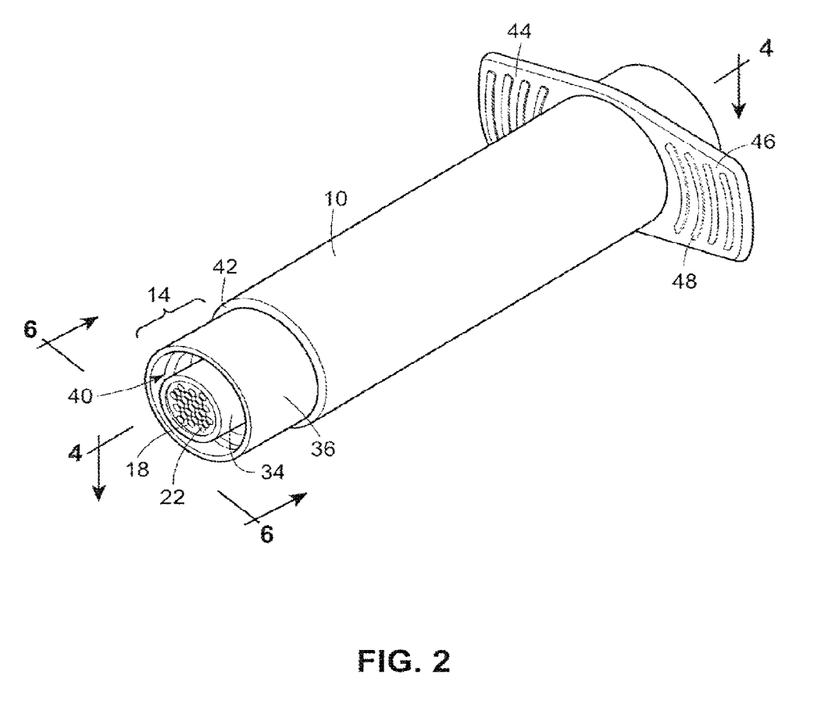
FIG. 2 is a perspective view of the male syringe barrel of FIG. 1.
Figure 4:
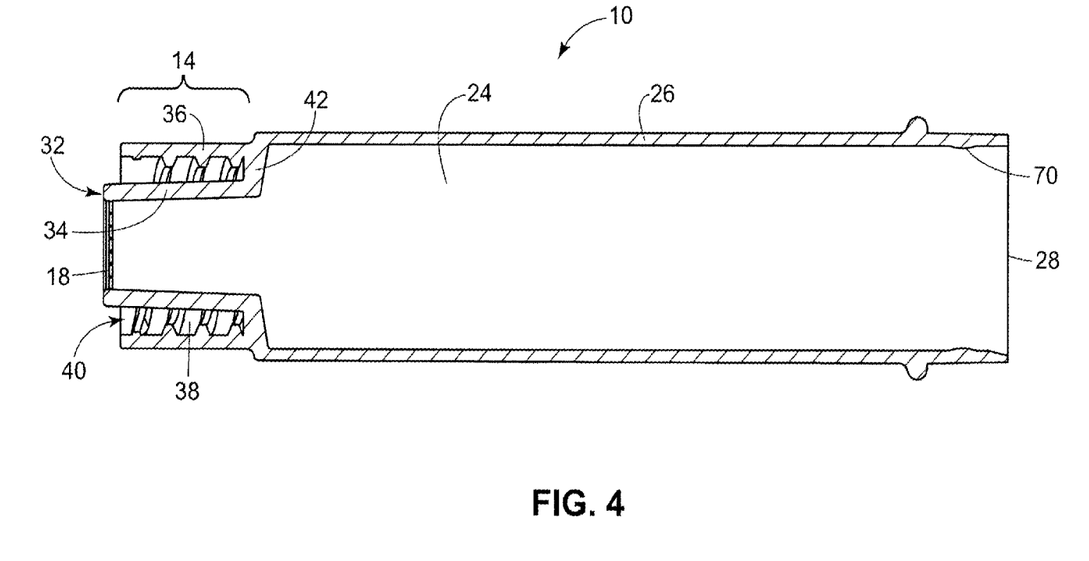
FIG. 4 is a cross-sectional view of the male syringe barrel of FIG. 2, taken along lines-4-4 of FIG. 2.
Figure 6:
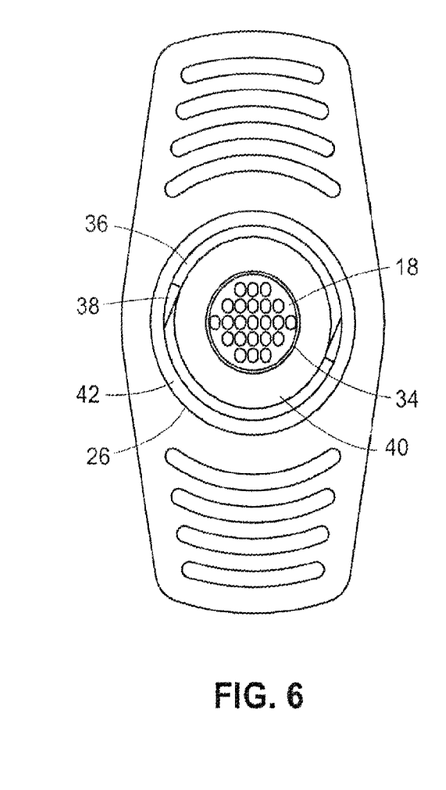
FIG. 6 is a plan view of the male syringe barrel of FIG. 2, taken along lines 6-6 of FIG. 2.

As best illustrated in FIGS. 2, 4 and 6, the first syringe barrel 10 includes a main chamber 24 defined by a cylindrical barrel wall 26, an open proximal end 28 sized to receive a plunger 30, and a distal end 32. The distal end 32 includes a screen 18. The axially-extending male engagement region 14 includes a cylindrical inner wall 34 and a cylindrical outer wall 36, separated from one another by at least one, and preferably two, female threads 38 forming a threaded channel 40 open at the distal end 32 of the first syringe barrel 10, radially outward of the screen 18. The inner wall 34 and outer wall 36 of the axially-extending male connecting region 14 come together at a neck portion 42 of the first syringe barrel 10.

A pair of opposing flanges 44, 46 project radially outwardly from the cylindrical barrel wall 26, preferably spaced a distance of approximately 0.3 inch from the proximal end 28 of the first syringe barrel 10. The flanges 44, 46 may each include a plurality of gripping ribs 48 on at least the surface of the flange facing the distal end 32 of the first syringe barrel 10.

Figure 3:
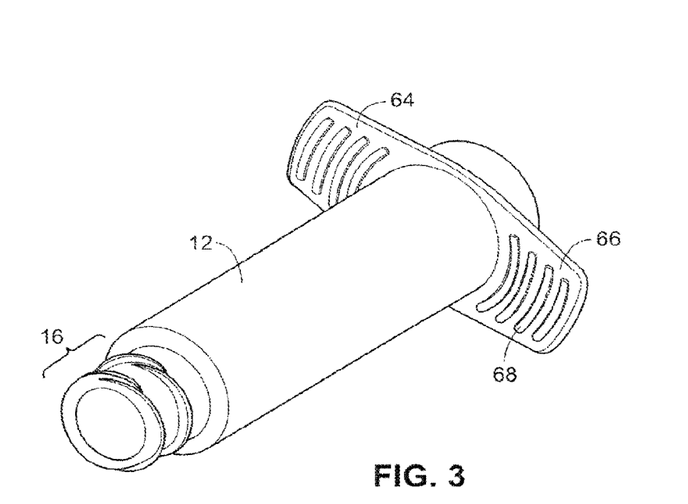
FIG. 3 is a perspective view of the female syringe barrel of FIG. 1.
Figure 3A:
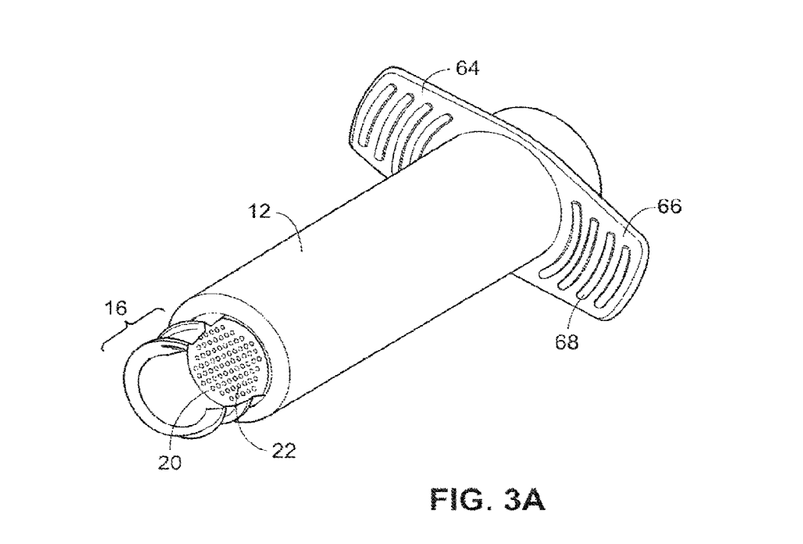
FIG. 3A is a perspective view of the female syringe barrel of FIG. 3, with a portion of an engagement region of the female syringe barrel cut away.
Figure 5:
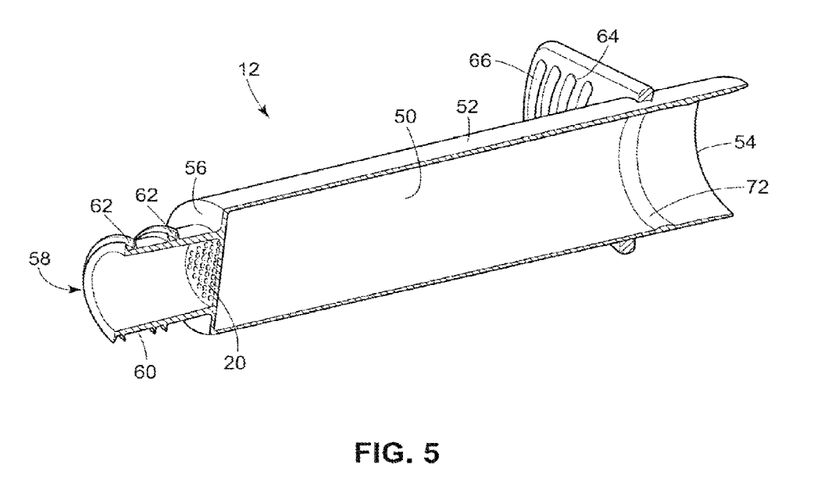
FIG. 5 is a cross-sectional view of the female syringe barrel of FIG. 3, taken along lines-5-5 of FIG. 3.
Figure 7:
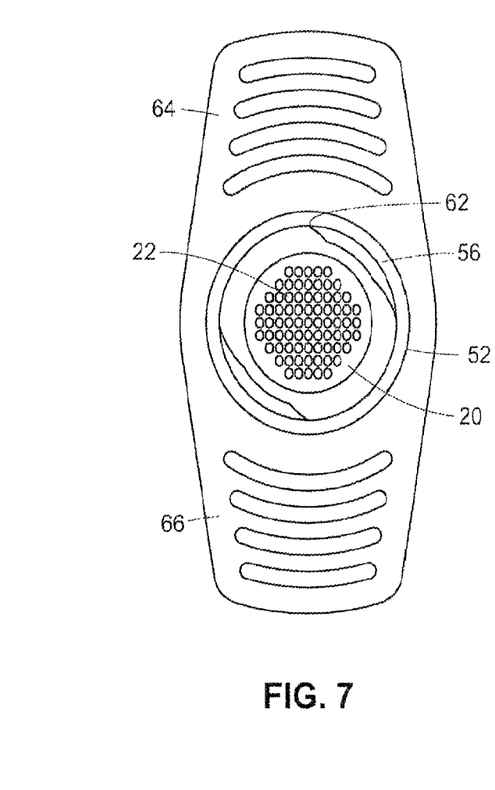
FIG. 7 is a plan view of the female syringe barrel of FIG. 3, taken along lines 7-7 of FIG. 3.

As best illustrated in FIGS. 3, 5 and 7, the second syringe barrel 12 includes a main chamber 50 defined by a cylindrical barrel wall 52. The cylindrical barrel wall 52 extends from an open proximal end 54 of the second syringe barrel 12 to a neck portion 56 near a distal end 58 of the second syringe barrel 12. The axially-extending female engagement region 16 extends distally of the neck portion 56. The screen 20 extends across the neck portion 56, separating the main chamber 50 of the second syringe barrel 12 from an interior of the female engagement region 16. The exterior of an axially-extending cylindrical wall 60 of the female engagement region 16 of the second syringe barrel 12 is provided with at least one, and preferably two, male threads 62. The male threads 62 are of a complementary pitch to the female threads 38 of the threaded channel 40 of the first syringe barrel 10.

A pair of opposing flanges 64, 66 project radially outwardly from the cylindrical barrel wall 52, preferably spaced a distance of approximately 0.3 inch from the proximal end 54 of the second syringe barrel 12. The flanges 64, 66 may each include a plurality of gripping ribs 68 on a side of the flange facing the distal end 58 of the second syringe barrel 12.

Figure 1:
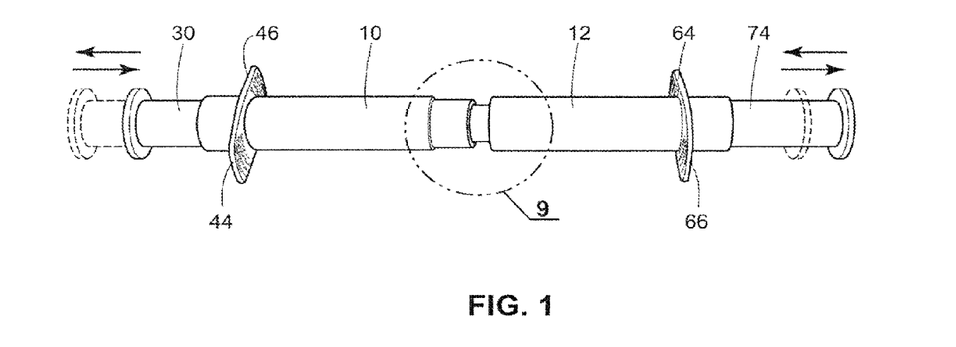
FIG. 1 is a perspective view of a male syringe barrel and a female syringe barrel of a first embodiment of the present disclosure, engaged with one another.
Figure 9:
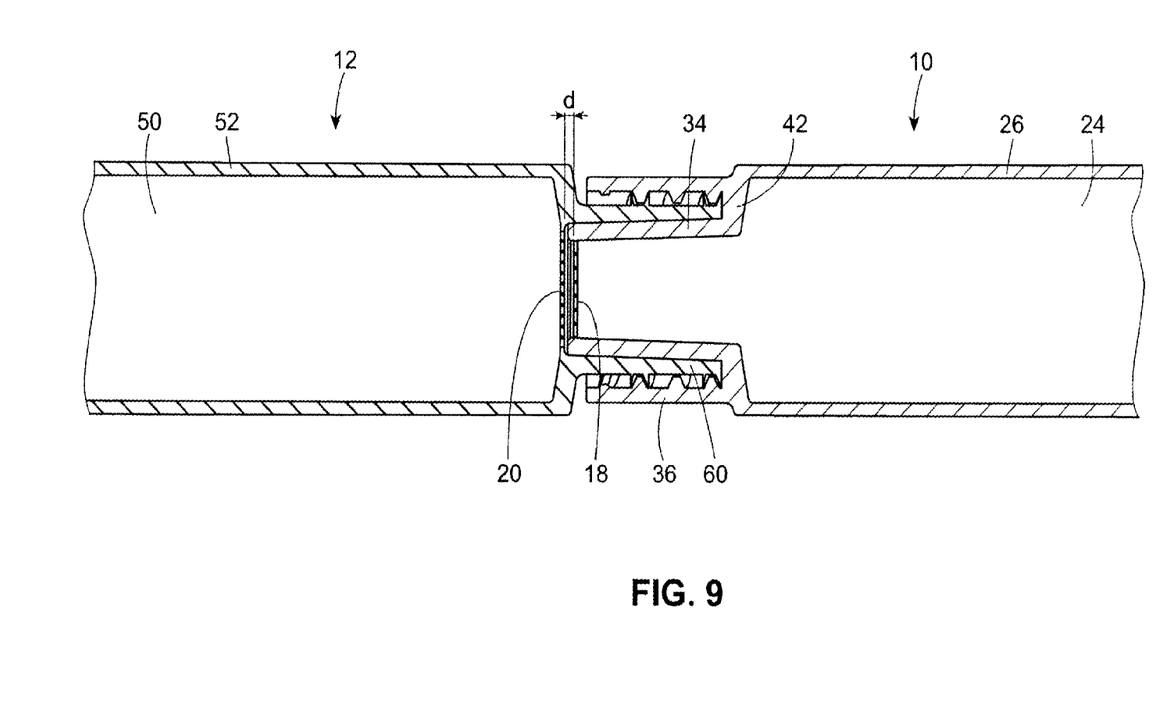
FIG. 9 is an enlarged cross-section view, broken away, of engagement regions of the male syringe barrel and the female syringe barrel of FIG. 1 when the syringe barrels are engaged with one another, taken along line 9 of FIG. 1.

When the first syringe barrel 10 and second syringe barrel 12 are engaged with one another as illustrated in FIGS. 1 and 9, the screen 18 of the first syringe barrel 10 and the screen 20 of the second syringe barrel 12 are in close proximity to one another. Preferably, when the first syringe barrel 10 and second syringe barrel 12 are engaged with one another, the screen 18 of the first syringe barrel 10 and the screen 20 of the second syringe barrel 12 are parallel to one another and spaced apart a distance d in a range from approximately 0.02 inch to 0.05 inch, preferably approximately 0.03 inch. It has been found that utilizing the two screens 18, 20 improves the mixing of syringe barrel contents, as compared to a single screen of conventional engageable syringe barrel mixing systems. Moreover, placing the screens 18, 20 in the separate syringe barrels 10, 12, as opposed to providing both screens at a distal end of a single syringe barrel, simplifies the molding process.

Figure 8:
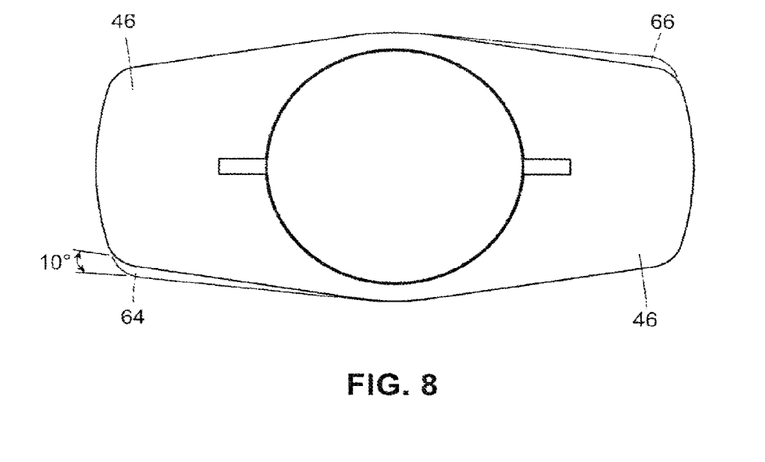
FIG. 8 is a top plan view of a male syringe barrel engaged with a female syringe barrel, illustrating alignment of the flanges of the respective syringe barrels when the syringe barrels are engaged with one another, and with broken lines indicating a preferred maximum angular off-set of the flanges of the respective syringe barrels.

The female threads 38 and the leading edges of the male threads 60, 62 are positioned such that when the first syringe barrel 10 and second syringe barrel 12 are fully engaged with one another, with the male engagement region 14 seated in the female engagement region 16, the flanges 44, 46 of the first syringe barrel 10 are substantially aligned with the flanges 64, 66 of the second syringe barrel 12. Preferably, when fully engaged, the flanges 64, 66 of the second syringe barrel 12 are no more than 10° out of alignment with the flanges 44, 46 of the first syringe barrel 10, as illustrated by the broken lines in FIG. 8 when the threads are fully threaded and fully torqued. In a preferred embodiment, the threads have a torque applied of approximately 2 lbf-in. when fully torqued.

Each of the first syringe barrel 10 and second syringe barrel 12 may include an integral annular retaining rib 70, 72 projecting inwardly from the cylindrical barrel wall 26, 52 of the respective syringe barrel, near the open proximal end 28, 54. Each of the annular retaining ribs 70, 72 serves to retain a sealing gasket of the plunger 30, 74 received in the respective syringe barrel.

In use, a given quantity of a substance to be reconstituted in powdered form, such as lyophilized thrombin, is provided in the second syringe barrel 12 with the plunger 74 received in the open proximal end 54 of the second syringe barrel 12, and a predetermined volume of a diluent or reconstituting agent, such as calcium chloride solution or liquid thrombin, is provided in the first syringe barrel 10 with the plunger 30 received in the open proximal end of the first syringe barrel 10 (although it will be recognized that the substance to be reconstituted may instead be initially provided in the first syringe barrel 10, and the diluent may be provided in the second syringe barrel 12). The screen 20 of the second syringe barrel 12 retains the powder in the main chamber 50 of the second syringe barrel 12 while the powder is dry. The first syringe barrel 10 and second syringe barrel 12 are then engaged with one another by inserting the male engagement region 14 of the first syringe barrel 10 into the female engagement region 16 of the second syringe barrel 12, with the male threads 62 extending outwardly from the axially-extending cylindrical wall 60 of the female engagement region 16 received in the female threads 38 of the threaded channel 40 of the male engagement region 14.

When the first syringe barrel 10 and second syringe barrel 12 are fully engaged with one another, the flanges 44, 46 of the first syringe barrel 10 are preferably substantially aligned with the flanges 64, 66 of the second syringe barrel 12. In order to mix the syringe barrel contents, initially the plunger 30 of the first syringe barrel 10, i.e. the syringe barrel having the diluent, is pushed to force the liquid into the second syringe barrel 12, the solid-bearing syringe barrel. The plunger 74 of the second syringe barrel 12 (which now also contains the diluent) is pushed to inject the mixture back across the two screens 18, 20 into the first syringe barrel 10. This process is repeated until the desired consistency is achieved. This is process of injecting the contents of one syringe barrel into another, then back into the first, is referred to as "swooshing". It is found that the force necessary to mix the contents of the two syringe barrels 10, 12 and the number of times the engaged syringe barrels 10, 12 must be swooshed to complete reconstitution is reduced, relative to conventional docking syringe barrels used for mixing or reconstituting their contents, and this is believed to be a benefit of the closely-spaced screens 18, 20. The size and concentration of the openings 22 also influences the efficiency with which the contents of the syringe barrels may be mixed. In addition, the homogeneous quality of the mixture is improved. As discussed in more detail below, alternate embodiments for the screens 18, 20, wherein the openings 22 take different shapes or forms, are contemplated within the scope of the present disclosure. In the present embodiment, the screens 18, 20 may be made using a mesh of material, such as "Polypropelene Plastic Mesh," McMaster-Carr part number 9265T41, having openings sized 0.021"×0.027".

Figure 10:
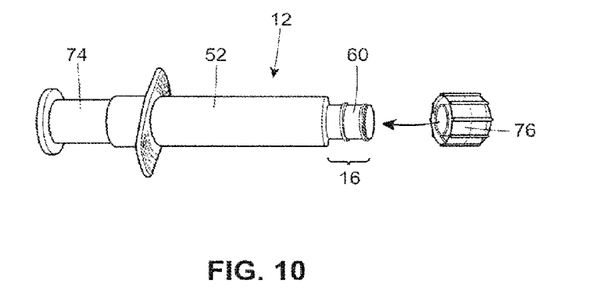
FIG. 10 is an exploded perspective view of the female syringe barrel of FIG. 3, with an adapter.
Figure 11:
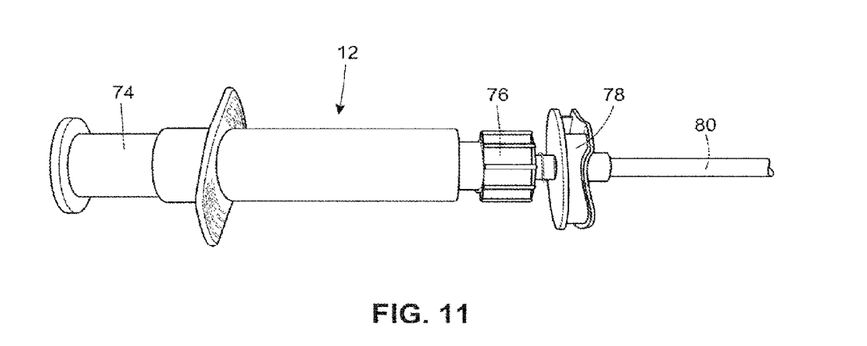
FIG. 11 is a perspective view of the syringe barrel and adapter of FIG. 10, in communication with a cannula handle and cannula, with a portion of the cannula broken away.

Once the contents of the syringe barrels 10, 12 are fully mixed, the syringe barrels 10, 12 are preferably tilted so the reconstituted solution is poured into the second syringe barrel 12. The syringe barrels 10, 12 are then disengaged from one another, and as illustrated in FIG. 10, an adapter 76 having an engagement region similar to the male engagement region 14 of the first syringe barrel 10, is secured to the female engagement region 16 of the second syringe barrel 12. Next, the adapter 76 may be connected to a conventional cannula handle 78 and cannula 80, as illustrated in FIG. 11. Utilizing a passageway or channel in a trocar, the cannula 80 may be introduced into the body of a patient adjacent a target tissue site. The plunger 74 on the second syringe barrel 12 may then be used to force the reconstituted solution into the cannula 80 and onto the target tissue site to act as a tissue sealant.

Figure 12:
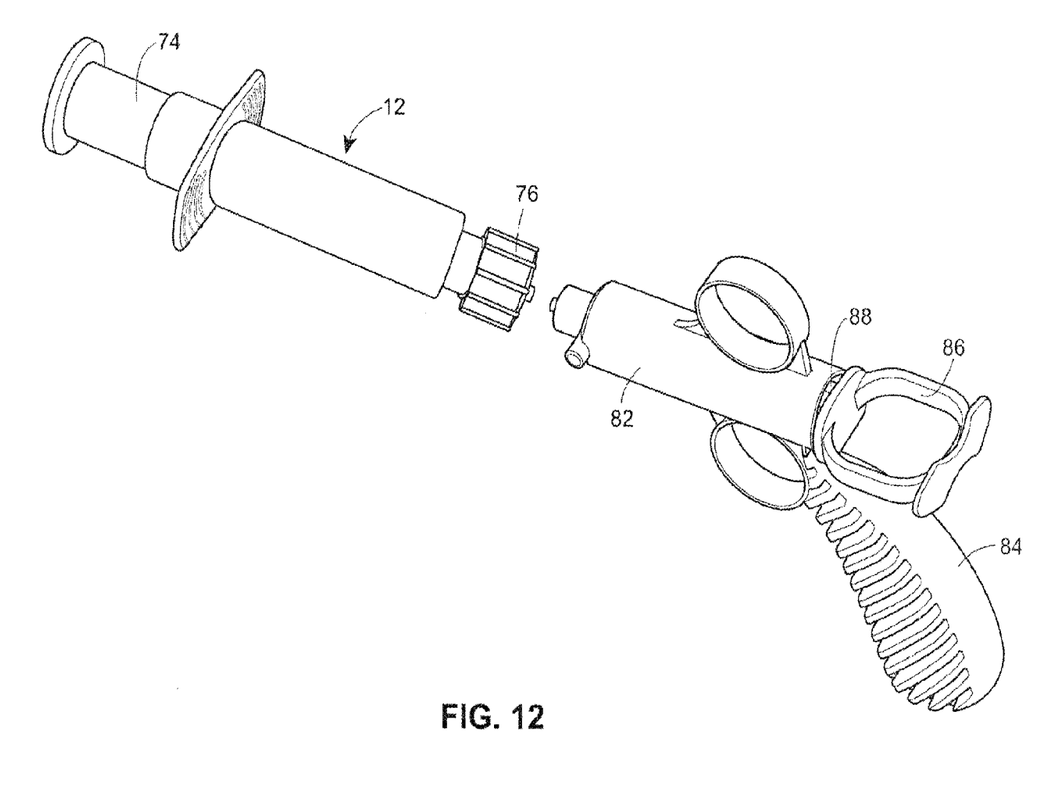
FIG. 12 is a perspective view of the syringe barrel and adapter of FIG. 10, in communication with a syringe barrel with integrated handle.
Figure 13:
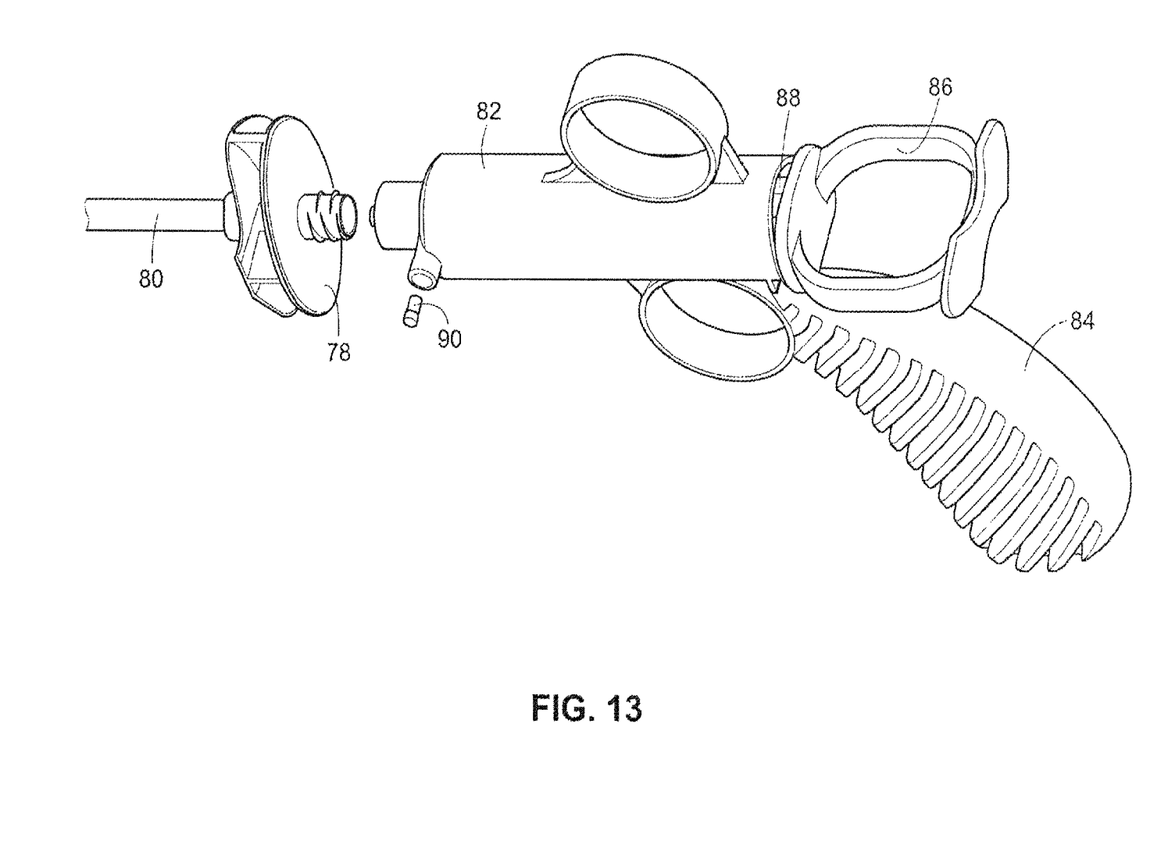
FIG. 13 is a perspective view of the syringe barrel with integrated handle of FIG. 12, with a cannula handle and cannula, with a portion of the cannula broken away.

As an alternative to connecting the second syringe barrel 12 and adapter 76 directly to the cannula handle 78 and cannula 80, the second syringe barrel 12 and adapter 76 may be attached to a syringe barrel 82 with an integrated handle 84, as illustrated in FIG. 12. The reconstituted contents of the second syringe barrel 12 may then be pushed into the syringe barrel 82 by pushing on the plunger 74 of the second syringe barrel 12. The syringe barrel 82 is preferably provided with a one-way check valve 90, as illustrated in FIG. 13. Once the reconstituted contents of the second syringe barrel 12 is pushed into the syringe barrel 82, the syringe barrel 82 is then detached from the second syringe barrel 12 and adapter 76, and connected to the cannula handle 78 and cannula 80. The syringe barrel 82 may then be used to introduce the reconstituted solution into the cannula by pressing on the stem 86, thereby advancing the plunger 88 into the syringe barrel 82, and thereby injecting the reconstituted solution into the cannula 80.

Depending on the length of the cannula 80, it may be necessary to introduce additional air into the cannula 80 behind the reconstituted solution in order to advance the reconstituted solution all the way through the cannula 80 and to a target tissue site. The one-way check valve 90 permits the medical professional, after the reconstituted solution has been introduced into the cannula 80, to pull back the stem 86 and plunger 88 a second time, thereby drawing air into the empty syringe barrel 82. The stem 86 and plunger 88 may then be advanced a second time, pushing the air into the cannula 80. This pressurizes the air in the cannula and the pressure then advances the reconstituted solution farther down the length of the cannula 80. The stem 86 and plunger 88 may be used to repeatedly draw air into the syringe 82 and advance the air into the cannula 80 until the desired amount of reconstituted solution is injected onto the target tissue site.

In knee surgeries and other surgical procedures where a target tissue site is readily accessible subcutaneously without a trocar, tissue sealant that has been reconstituted using the system of the present disclosure may be applied to the internal target tissue site directly from either the syringe barrel 82 or the second syringe barrel 12, without the use of a cannula 80.

Figure 14:
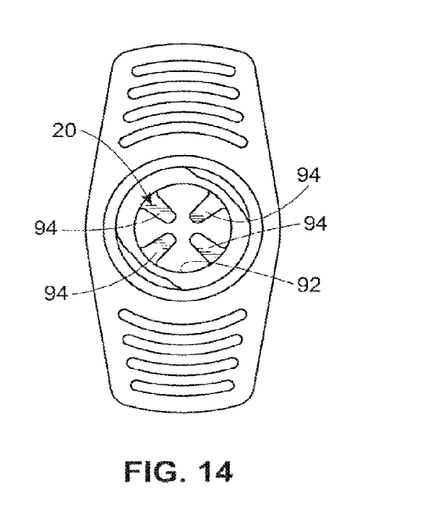
FIG. 14 is a plan view of a male syringe barrel similar to FIG. 6, illustrating a screen of a first alternate embodiment of the present disclosure.

In some instances, it has been found that portions of mesh screens 18, 20 may become clogged, thereby increasing the resistance to flow. However, enlarging the size of the openings in the mesh may detrimentally affect mixing efficiency. Balancing these considerations, alternate screen designs are also contemplated within the scope of the present disclosure. Turning to FIGS. 14-18, the screens 18, 20 of the first and second syringe barrels 10, 12 may have forms other than a mesh. For instance, as illustrated in FIG. 14, a first alternate embodiment of the screen 20 of the second syringe barrel 12 may take the form of a circular opening 92 having a plurality of spaced, inwardly-directed protuberances or bumps 94. The inwardly-directed protuberances or bumps 94 may be arranged with each of four bumps 94 disposed at 45° intervals along the interior of the circular opening 92.

Figure 15:
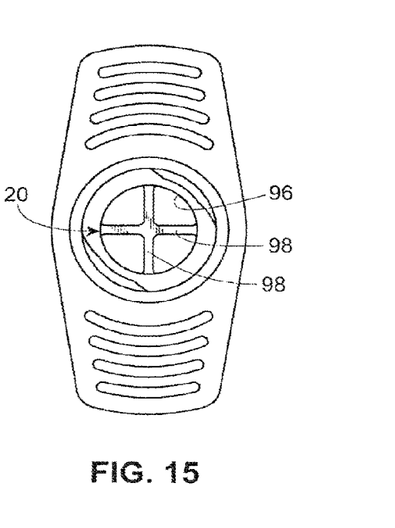
FIG. 15 is a plan view of a male syringe barrel similar to FIG. 6, illustrating a screen of a second alternate embodiment of the present disclosure.

As illustrated in FIG. 15, a second alternate embodiment of the screen 20 may take the form of a circular opening 96 provided with a pair of bar-like elements 98 arranged in a cross configuration.

Figure 16:
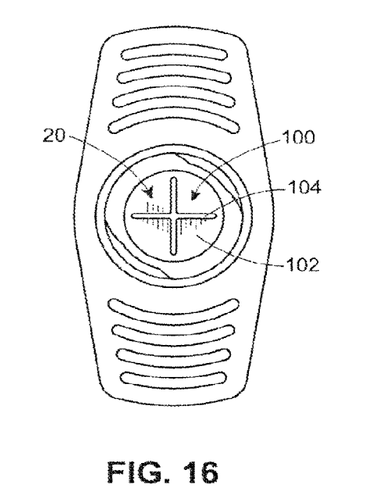
FIG. 16 is a plan view of a male syringe barrel similar to FIG. 6, illustrating a screen of a third alternate embodiment of the present disclosure.

As illustrated in FIG. 16, a third alternate embodiment of the screen 20 may take the form of a disc 100 having a plurality of cantilevered wedges or flaps 102 defining slots therebetween. In this particular embodiment, four flaps 102 are provided, defining four slots 104 in the disc 100. In a particularly preferred embodiment, each of the slots 104 has a length of approximately 0.377" and a width of approximately 0.015", yielding a cross-sectional flow area of approximately 0.011085 in$^2$.

Figure 17:
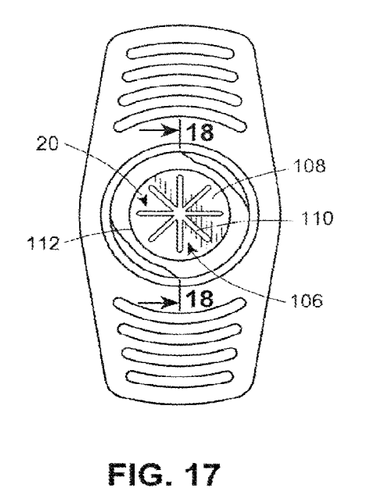
FIG. 17 is a plan view of a male syringe barrel similar to FIG. 6, illustrating a screen of a fourth alternate embodiment of the present disclosure.

In FIG. 17, a fourth alternate embodiment of the screen 20 is illustrated. In this embodiment, the screen 20 takes the form of a disc 106 having eight cantilevered wedges or flaps 108, defining eight slots 110 in the disc 106. In a particularly preferred embodiment, each of the slots 110 has a length of approximately 0.377" and a width of approximately 0.015", yielding a cross-sectional flow area of approximately 0.021945 in$^2$.

It is recognized that the number and dimensions of the slots 104, 110 in the third and fourth alternate embodiments of the screen 20 will impact the degree to which any retained powder in the main chamber 50 of the second syringe barrel 12 will break apart and mix upon initial and subsequent tilting back-and-forth of the engaged first and second syringe barrels 12. The number and dimensions of the slots 104, 110 will also determine the effectiveness of retention of dry powder in the main chamber 50 when the second syringe barrel 12 is uncapped. Thus, variations on the geometry described for these particular preferred embodiments may be made that are still considered within the scope of the present disclosure.

Figure 18:
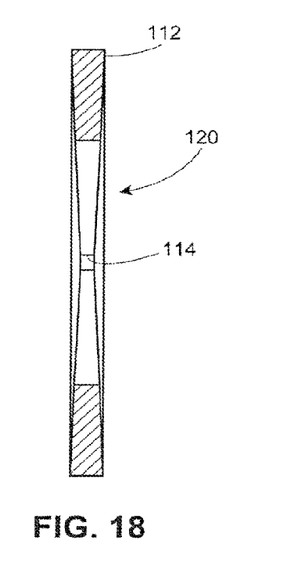
FIG. 18 is a cross-sectional view of the screen of the male syringe barrel of FIG. 17, taken along lines 18-18 of FIG. 17.

As illustrated in the cross-sectional view of FIG. 18, the cantilevered wedges or flaps 108 of the fourth alternate embodiment (and, similarly, the cantilevered wedges or flaps 102 of the third alternate embodiment) may be of a thickness that tapers from a perimeter 112 of the screen 20 toward a tip 114 of each of the flaps 108. By tapering the flaps 108 of the screen 20, the flaps 108, which are preferably plastic, are free to bend in the direction of flow during mixing. By virtue of the flaps 108 bending in the direction of flow, the slots 110 increase in width during each pour across the screen 20, thereby reducing the resistance to flow.

While the present invention has been described with respect to various specific embodiments, it will be understood that variations may be made that are still within the scope of the present disclosure. The appended claims are not intended to be limited to the details of the specific embodiments disclosed herein.

What is claimed is:

1. A method for reconstituting a powdered agent comprising:
   providing a first syringe barrel including a main chamber defined by a cylindrical barrel wall, an open proximal end, and a male engagement region at a distal end, the male engagement region including a first screen, wherein the first screen comprises
   a first plurality of cantilevered wedges, each of the first plurality of cantilevered wedges having a single pointed tip;
   wherein each of the first plurality of cantilevered wedges has a thickness along a longitudinal axis of the first syringe barrel that tapers, with the thickness of the cantilevered wedge along the longitudinal axis of the first syringe barrel decreasing from a perimeter of the first screen to the pointed tip of the cantilevered wedge;
   wherein a first screen slot is defined between each pair of the first plurality of cantilevered wedges; and
   wherein each of the first plurality of cantilevered wedges is configured to bend in a direction of flow of solution across the first screen and each of the first screen slots increases in width during flow of solution across the first screen;

providing a second syringe barrel including a main chamber defined by a cylindrical barrel wall, an open proximal end, and a female engagement region at a distal end, the female engagement region including a second screen, wherein the second screen comprises a second plurality of cantilevered wedges, each of the second plurality of cantilevered wedges having a single pointed tip;

wherein each of the second plurality of cantilevered wedges has a thickness along a longitudinal axis of the second syringe barrel that tapers, with the thickness of the cantilevered wedge along the longitudinal axis of the second syringe barrel decreasing from a perimeter of the second screen to the pointed tip of the cantilevered wedge;

wherein a second screen slot is defined between each pair of the second plurality of cantilevered wedges; and wherein each of the second plurality of cantilevered wedges is configured to bend in a direction of flow of solution across the second screen and each of the second screen slots increases in width during flow of solution across the second screen;

depositing the powdered agent into the main chamber of one of the first syringe barrel or the second syringe barrel;

inserting a plunger in the open proximal end of the first syringe barrel;

inserting a plunger in the open proximal end of the second syringe barrel;

drawing a diluent into the main chamber of one of the first syringe barrel or the second syringe barrel;

engaging the male engagement region of the first syringe barrel with the female engagement region of the second syringe barrel; and tilting the engaged first and second syringe barrels back and forth to mix the powdered agent and diluent to form a mixture.

2. The method of claim 1, wherein in providing the first syringe barrel, the first syringe barrel includes a neck portion and the male engagement region includes a cylindrical inner wall and a cylindrical outer wall, each of the cylindrical inner and outer walls axially extending in a distal direction from the neck portion and defining a threaded channel therebetween and the first screen extends radially inwardly from the cylindrical inner wall.

3. The method of claim 1, wherein in providing the second syringe barrel, the second syringe barrel includes a neck portion, the female engagement region includes an axially extending cylindrical wall including at least one male thread on an outer surface thereof, and the second screen extends radially inwardly from the axially extending cylindrical wall of the second syringe barrel.

4. The method of claim 1, wherein in providing each of the first syringe barrel and the second syringe barrel, each of the first syringe barrel and second syringe barrel includes a pair of flanges projecting radially outwardly therefrom, and in engaging the male engagement region of the first syringe barrel with the female engagement region of the second syringe barrel, substantially aligning the pair of flanges projecting radially from the first syringe barrel with the pair of flanges projecting radially from the second syringe barrel when the first syringe barrel and the second syringe barrel are fully engaged with one another.

5. The method of claim 1, wherein in tilting the engaged first and second syringe barrels back and forth, expanding the width of the slots between each pair of the first plurality of adjacent cantilevered wedges and expanding the width of the slots between each pair of the second plurality of adjacent cantilevered wedges.

6. The method of claim 1, further comprising, after tilting the engaged first and second syringe barrels back and forth:

tilting the engaged first and second syringe barrels so that the mixture is disposed in the second syringe barrel;

disengaging the first and second syringe barrels; and attaching an adapter to the female engagement region of the second syringe barrel.

* * * * *